US012351846B2

(12) United States Patent
Lee et al.

(10) Patent No.: US 12,351,846 B2
(45) Date of Patent: Jul. 8, 2025

(54) MICROORGANISM FOR PRODUCING L-AMINO ACID HAVING INCREASED CYTOCHROME C ACTIVITY, AND L-AMINO ACID PRODUCTION METHOD USING SAME

(71) Applicant: CJ CheilJedang Corporation, Seoul (KR)

(72) Inventors: Han Hyoung Lee, Seoul (KR); Sang Min Park, Seoul (KR); Hyun Won Bae, Seoul (KR); Hyo Jeong Byun, Seoul (KR); Yong Uk Shin, Seoul (KR); Boram Lim, Seoul (KR); Jaewon Jang, Seoul (KR); Moo Young Jung, Seoul (KR); Yunjung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 209 days.

(21) Appl. No.: 17/605,671

(22) PCT Filed: Dec. 22, 2020

(86) PCT No.: PCT/KR2020/018896
§ 371 (c)(1),
(2) Date: Oct. 22, 2021

(87) PCT Pub. No.: WO2021/133030
PCT Pub. Date: Jul. 1, 2021

(65) Prior Publication Data
US 2022/0275412 A1 Sep. 1, 2022

(30) Foreign Application Priority Data
Dec. 23, 2019 (KR) .................. 10-2019-0173087
Dec. 23, 2019 (KR) .................. 10-2019-0173088

(51) Int. Cl.
C12P 13/08 (2006.01)
C07K 14/32 (2006.01)
C12N 1/20 (2006.01)
C12N 15/77 (2006.01)
C12R 1/15 (2006.01)

(52) U.S. Cl.
CPC ............. *C12P 13/08* (2013.01); *C07K 14/32* (2013.01); *C12N 1/205* (2021.05); *C12N 15/77* (2013.01); *C12N 2800/101* (2013.01); *C12R 2001/15* (2021.05)

(58) Field of Classification Search
CPC .................................................. C12P 13/08
See application file for complete search history.

(56) References Cited

U.S. PATENT DOCUMENTS

2002/0048795 A1* 4/2002 Farwick et al. ........ C12P 13/08
435/115
2004/0014180 A1 1/2004 Bott et al.

FOREIGN PATENT DOCUMENTS

| EP | 0869175 | 10/1998 |
|----|---------|---------|
| EP | 2067864 | 6/2009 |
| KR | 10-2021-0080975 | 7/2021 |
| WO | 2006-065095 | 6/2006 |

OTHER PUBLICATIONS

Bengtsson et al. Bacillus subtilis Contains Two Small c-Type Cytochromes with Homologous Heme Domains but Different Types of Membrane Anchors. J Biol Chem 1999, vol. 274(37): pp. 26179-26184. (Year: 1999).*
Janto et al. The genome of alkaliphilic Bacillus pseudofirmus OF4 reveals adaptations that support the ability to grow in an external pH range from 7.5 to 11.4. Environ Microbiol, 2011, vol. 13(12): pp. 3289-3309. (Year: 2011).*
Rosner. Control of Lysine Biosynthesis in Bacillus subtilis: Inhibition of Dianminopimelate Decarboxylase by Lysine. J Bacteriol, 1975, vol. 121(1): pp. 20-28. (Year: 1975).*
Srivastava, Preeti, and J. K. Deb. "Gene expression systems in corynebacteria." Protein expression and purification 40.2 (2005): 221-229. (Year: 2005).*
NCBI. GenBank accession No. ADC50799.1, Jan. 30, 2014.
NCBI. GenBank accession No. ADC49161.1, Jan. 30, 2014.
Kabus, A. et al. "Role of Cytochrome bd Oxidase from Corynebacterium glutamicum in Growth and Lysine Production", Applied and Environmental Microbiology. vol. 73, No. 3, pp. 861-868, Feb. 2007.
Van der Rest et al., "A heat shock following electroporation induces highly efficient transformation of Corynebacterium glutamicum with xenogeneic plasmid DNA", Appl. Microbiol. Biotechnol. 52:541-545, Oct. 1999.
Samuel Karlin et al., "Applications and statistics for multiple high-scoring segments in molecular sequences", Proc. Natl. Acad. Sci. USA vol. 90, pp. 5873-5877, Jun. 1993.
William R. Pearson, "Rapid and Sensitive Sequence Comparison with FASTP and FASTA", Methods Enzymol., 183, 63, 1990.
Sambrook et al., "Labeling 3 ' Termini of Double-stranded DNA Using the Klenow Fragment of *E. coli* DNA Polymerase I", Molecular Cloning (a laboratory manual) third edition, 2001.
Bott, Michael, et al. "The respiratory chain of Corynebacterium glutamicum." Journal of Biotechnology 104.1-3 (Sep. 4, 2003): 129-153.
Edited by Zhang Huikang, "Trial Textbook for Light Industry Major in Secondary Specialized Schools Microbiology (for industrial fermentation major)" Beijing: China Light Industry Press Ltd, First printed in Apr. 1990, 5th reprinted in Apr. 1997, pp. 171-174, ISBN 7-5019-0777-3.

(Continued)

*Primary Examiner* — Robert J Yamasaki
*Assistant Examiner* — Trevor Kane
(74) *Attorney, Agent, or Firm* — LEX IP MEISTER, PLLC

(57) ABSTRACT

Provided are a microorganism for producing L-amino acid, having increased cytochrome C activity, and an L-amino acid production method using the microorganism.

6 Claims, 1 Drawing Sheet

Specification includes a Sequence Listing.

(56) References Cited

OTHER PUBLICATIONS

Rospatent, Office Action of RU 2021136492 dated Jun. 15, 2023.
NCBI Reference Sequence: WP_012960434.1, Dec. 14, 2017. Cytochrome c [Bacillus pseudofirmus]. Found online: https://www.ncbi.nlm.nih.gov/protein/502725450?sat=48&satkey=58976493, Jun. 15, 2023.
Pierre Broun et al., "Catalytic Plasticity of Fatty Acid Modification Enzymes Underlying Chemical Diversity of Plant Lipids," Science, vol. 282, No. 5392, pp. 1315-1317, Nov. 1998, doi: https://doi.org/10.1126/science.282.5392.1315.
Jennifer L. Seffernick et al., "Melamine Deaminase and Atrazine Chlorohydrolase: 98 Percent Identical but Functionally Different," Journal of Bacteriology, vol. 183, No. 8, pp. 2405-2410, Apr. 2001, doi: https://doi.org/10.1128/jb.183.8.2405-2410.2001.
James C. Whisstock et al., "Prediction of protein function from protein sequence and structure," Quarterly Reviews of Biophysics, vol. 36, No. 3, pp. 307-340, Aug. 2003, doi: https://doi.org/10.1017/s0033583503003901.
Andrzej Witkowski et al., "Conversion of a β-Ketoacyl Synthase to a Malonyl Decarboxylase by Replacement of the Active-Site Cysteine with Glutamine," Biochemistry, vol. 38, No. 36, pp. 11643-11650, Aug. 1999, doi: https://doi.org/10.1021/bi990993h.
SIPO, Office Action of CN 202080045751.9 dated Oct. 17, 2023.
EPO, search report of EP 20905486.5 dated May 6, 2024.
Benjamin Janto et al., "Genome of alkaliphilic Bacillus pseudofirmus OF4 reveals adaptations that support the ability to grow in an external pH range from 7.5 to 11.4", Environmental Microbiology (2011) 13(12), 3289-3309, doi: 10.1111/j.1462-2920.2011.02591.x. Epub Sep. 27, 2011.
Elisete P. Rodrigues et al., "Identification of Genes Involved in Indole-3-Acetic Acid Biosynthesis by Gluconacetobacter diazotrophicus PAL5 Strain Using Transposon Mutagenesis", Front. Microbiol., vol. 7, article 1572, Oct. 7, 2016.
Rospatent, Acceptance decision of RU 2021136492 dated Apr. 1, 2024.
NCBI Reference Sequence: WP_012958161.1, May 26, 2013. Cytochrome C551 [Bacillus pseudofirmus]. Found online: https://www.ncbi.nlm.nih.gov/protein/502723177?sat=21&satkey=58939752. Application date Jun. 15, 2023.

* cited by examiner

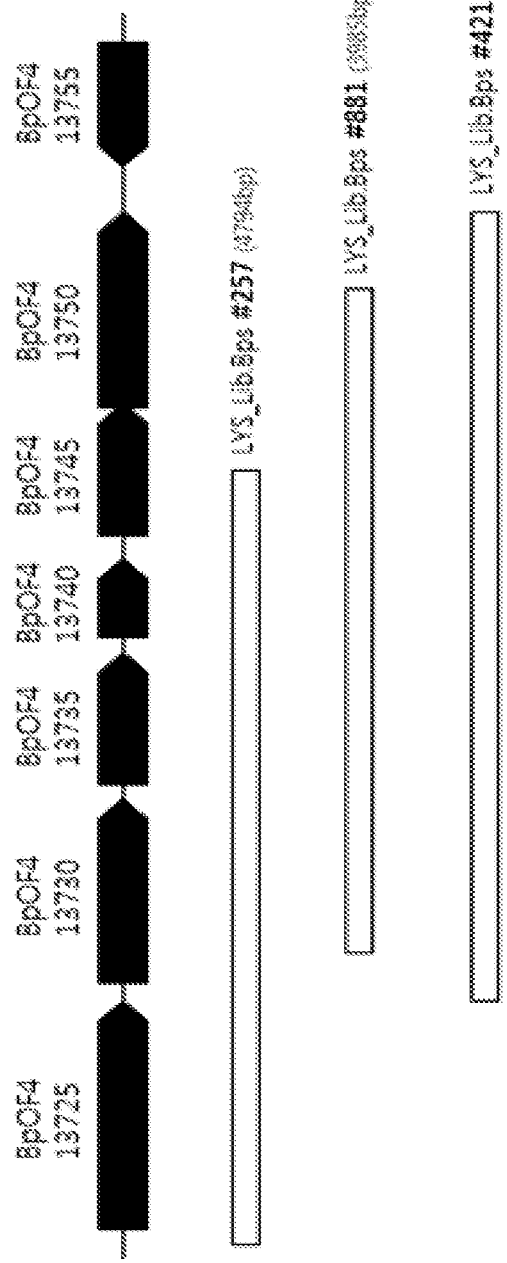

MICROORGANISM FOR PRODUCING L-AMINO ACID HAVING INCREASED CYTOCHROME C ACTIVITY, AND L-AMINO ACID PRODUCTION METHOD USING SAME

TECHNICAL FIELD

Cross-Reference to Related Applications

This application claims the benefit of KR 1 0-201 9-01 73087 and KR 10-2019-0173088 filed on Dec. 23, 2019 with the Korean Intellectual Property Office, the entire disclosure of which is herein incorporated by reference Provided are an L-amino acid producing microorganism having enhanced cytochrome C activity and an L-amino acid producing method using same.

Background Art

Microorganisms belonging to the genus of *Corynebacterium* are Gram-positive and have been widely used in the production of L-amino acids. L-amino acids, especially L-lysine, find applications in the animal feed industry and the human medical and cosmetic industries. For industrial applications, L-amino acids are, for the most part, produced by fermentation using *Corynebacterium* strains.

Many attempts have been made to improve L-amino acid producing methods using *Corynebacterium* spp. strains. Among them are studies on recombinant DNA technology by which specific genes are manipulated to knockdown or attenuated expression to produce L-amino acids. In addition, there have been studies in which each of genes involved in L-amino acid biosynthesis is amplified and analyzed for effect on L-amino acid production, thereby modifying L-amino acid producing *Corynebacterium* strains.

In the industry of producing lysine through fermentation, production of a high concentration of lysine and improved lysine production potentials of microorganisms are important factors. Accordingly, efforts have been continued to potentiate lysine production potentials of microorganisms and to steadily maintain improved lysine production potentials during fermentation culture. However, it is difficult to maintain a lysine production potential to the late phase of cultivation due to various internal and external factors inhibitory of microbial activity.

Therefore, there is still a need for development of a strain in which an L-lysine production potential is improved and can be steadily maintained.

DISCLOSURE

Technical Problem

An embodiment provides an L-amino acid producing microorganism having enhanced cytochrome C activity. For example, the enhancement of cytochrome C activity may be achieved by introducing a cytochrome C coding gene. For example, the cytochrome C coding gene may be an exogenous gene.

Another embodiment provides a method of producing an L-amino acid, the method comprising a step of culturing the L-amino acid producing microorganism.

A further embodiment provides a composition for producing an L-amino acid or improving L-amino acid production in a microorganism, the composition comprising a cytochrome C coding gene, a recombinant vector carrying the gene, or both of them.

Technical Solution

Suggested according to an embodiment provided herein is a strain modification technology for amino acid production on the basis of investigating how the amplification of a gene involved in lysine production of *Corynebacterium* spp. microorganisms affects a lysine production potential thereof. Generally, strategies for increasing production potentials of amino acids such as lysine and the like include improving production yields of amino acids such as lysine, etc. or increasing outputs of amino acids such as lysine, etc. per unit time (productivity). Specially, the amino acid productivity for lysine, etc. may be affected by various factors comprising components of fermentation media, osmotic pressures of fermentation media, stirring speeds, oxygen supply rates, etc. Over a culturing period of time, microorganisms steadily decrease in lysine production potential and cellular activity due to problems, for example, stress put by various substances and metabolites present in fermentation broth, oxygen depletion attributed to the increase of microbial mass, physical conditions such as temperature and stirring speed. According to an embodiment of the present disclosure, a strain modification technology is provided for overcoming the stress put by such various factors and for allowing the microorganisms to retain a constant production activity for target products to the late phase of cultivation.

Below, a detailed description will be given of the present disclosure.

An embodiment provides an L-amino acid producing microorganism having enhanced cytochrome C activity.

The term "L-amino acid producing microorganism", as used herein, may refer to a microorganism that has an L-amino acid production potential, which is increased by enhancing cytochrome C activity therein, compared to before and/or is generated from a null activity by enhancing cytochrome C activity therein. The term "microorganism", as used herein, may be intended to encompass unicellular bacteria and can be used interchangeably with "cell".

The L-amino acid may be L-lysine.

Herein, a microorganism before enhancement of cytochrome C activity may be expressed as a host microorganism in order to discriminate from "L-amino acid producing microorganism" that has an L-amino acid production potential enhanced or generated by enhancing cytochrome C activity.

In a specific embodiment, the host microorganism may be any microorganism having an L-amino acid (e.g., L-lysine) production potential. In a specific embodiment, the host microorganism may be a microorganism in which an L-lysine production potential naturally occurs or is generated by introducing a mutation into a parent strain that originally lacks or is remarkably poor in L-lysine production potential.

In a specific embodiment, the host microorganism may be any Gram-positive bacteria in which an L-lysine production potential naturally occurs or is generated by introducing a mutation into a parent strain that originally lacks or is remarkably poor in L-lysine production potential and, for example, may be selected from the group consisting of microorganisms of the genus *Corynebacterium* and microorganisms of the genus *Escherichia*. Examples of the microorganisms of the genus *Corynebacterium* may include *Corynebacterium glutamicum, Corynebacterium ammoniagenes, Brevibacterium lactofermentum, Brevibacterium flavum, Corynebacterium thermoaminogenes*, and *Corynebacterium efficiens*, but are not limited thereto. For example, the microorganism of the genus *Corynebacterium* may be *Corynebacterium glutamicum*.

As used herein, the term "cytochrome C" may refer to a membrane-binding monomeric cytochrome C that is derived from bacteria, has an average molecular weight of 15 kDa or less, for example, about 8 kDa to about 15 kDa, and/or ranges in length from 90 to 150 amino acids, 100 to 150 amino acids, 120 to 150 amino acids, 90 to 125 amino acids, 100 to 125 amino acids, or 120 to 125 amino acids. In an embodiment, the cytochrome C may be derived from microorganisms of genus *Bacillus* and may be at least one selected from the cytochrome C family of proteins that show the lowest energy absorption band (absorbance) at a wavelength of 550-555 nm or 550 to 551 nm in their reduced state. In an embodiment, the cytochrome C may comprise at least one, for example, one, two, or three proteins selected from the group consisting of cytochrome C-551 (absorbance at about 551 nm) and cytochrome C-550 (absorbance at about 550 nm), both derived from a microorganism of genus *Bacillus* (the numerals suffixed to cytochrome C means a wavelength at which the cytochrome C exhibits the wavelength in its reduced state). The microorganism of the genus *Bacillus* may one or more selected from the group consisting of *Bacillus pseudofirmus, Bacillus subtilis*, and the like.

In a specific embodiment, the cytochrome C, for example, at least one selected from cytochrome C-551 and cytochrome C-550 may comprise an amino acid sequence encoded by cccA or cccB. In an embodiment, the cytochrome C may be at least one selected from the group consisting of cytochrome C-551 derived from *Bacillus pseudofirmus* (e.g., *Bacillus pseudofirmus* OF4, etc.) and/or *Bacillus subtilis*, and cytochrome C-550 derived from *Bacillus subtilis*, and the like.

In greater detail, the cytochrome C (e.g., *Bacillus subtilis*-derived cytochrome C-551) may comprise a polypeptide comprising an amino acid sequence (e.g., SEQ ID NO: 16) encoded by cccA (e.g., BpOF4_13740 derived from *Bacillus pseudofirmus* OF4), a polypeptide comprising an amino acid sequence (e.g., SEQ ID NO: 27) encoded by cccB (e.g., BpOF4_05495 derived from *Bacillus pseudofirmus* OF4), or both of them.

Unless defined otherwise, the cytochrome C described herein is construed to refer to any protein having a sequence identity of 20% or greater, 30% or greater, 40% or greater, 50% or greater, 55% or greater, 60% or greater, 65% or greater, 70% or greater, 75% or greater, 80% or greater, 82% or greater, 85% or greater, 87% or greater, 90% or greater, 91% or greater, 92% or greater, 93% or greater, 94% or greater, 95% or greater, 96% or greater, 97% or greater, 98% or greater, or 99% or greater (e.g., 60% to 99.5%, 70% to 99.5%, 80% to 99.5%, 85% to 99.5%, 90% to 99.5%, 91% to 99.5%, 92% to 99.5%, 93% to 99.5%, 94% to 99.5%, 95% to 99.5%, 96% to 99.5%, 97% to 99.5%, 98% to 99.5%, or 99% to 99.5%) with the amino acid sequence of SEQ ID NO: 16 or 27.

As such, the proteins having the sequence identity falling within the scope of the cytochrome C described herein may be one having:

(1) at least one of the aforementioned characteristics of cytochrome C, for example, selected from (a) bacterial origin, (b) an average molecular weight of 15 kDa or less, for example, about 8 kDa to about 15 kDa, and/or a length of 90 to 150, 100 to 150, 120 to 150, 90 to 125, 100 to 125, or 120 to 125 amino acid residues, (c) a membrane binding property, and (d) a monomeric property, and/or (2) an effect attributed to the activity enhancement in the microorganism having (e) an increase in L-amino acid (e.g., L-lysine) production potential, and/or (f) an increase in sugar consumption rate, compared to non-modified microorganisms, wherein the increases are equivalent to those having the amino acid sequences of SEQ ID NO: 16 or 27.

In a specific embodiment, the L-amino acid producing microorganism having enhanced cytochrome C activity may have an increased L-amino acid production potential, compared to non-modified microorganisms of the same species, which were not modified in order to enhance cytochrome C activity.

As used herein, the term "enhancement of cytochrome C activity" may refer to any manipulation in a microorganism to enhance cytochrome C activity therein, compared to the intrinsic activity or pre-manipulation activity of the microorganism, comprising introduction of cytochrome C activity into the microorganism. The "introduction" may refer an action by which cytochrome C activity is naturally or artificially generated in a microorganism which originally lacks cytochrome C activity. The term "non-modified microorganism" may refer to a host microorganism in which cytochrome C activity is not enhanced (e.g., a host microorganism which is not modified for enhancing the cytochrome C activity) or a host microorganism that has not yet undergone the enhancement of cytochrome C activity. The term "intrinsic activity" may refer to the cytochrome C activity that is retained by a host microorganism in which cytochrome C activity is not enhanced or by a host microorganism that has not yet undergone the enhancement of cytochrome C activity. In this context, the term "non-modified" can be used to the same meaning as the state in which genetic modification is not induced, with intrinsic activity being retained.

For example, the enhancement of cytochrome C activity may be achieved by introducing exogenous cytochrome C or by strengthening intrinsic cytochrome C activity. In a specific embodiment, the enhancement of cytochrome C activity may be achieved by introducing exogenous cytochrome C.

In a specific embodiment, the enhancement of cytochrome C activity in a microorganism may be accounted for by an increase in sugar consumption rate in the microorganism, compared to non-modified microorganisms in which cytochrome C activity is not enhanced. Particularly, a cytochrome C activity-enhanced microorganism illustrated in a specific embodiment may be similar to the non-modified microorganism with respect to growth rate (OD value) and/or L-amino acid, e.g., L-lysine production yield within a particular period of growth, but show an increased sugar consumption rate, compared to the non-modified microorganism, which suggests that the cytochrome C activity-enhanced microorganism produces a larger amount of an L-amino acid within a shorter time, compared to non-modified microorganisms, thereby showing improved L-amino acid productivity.

In an embodiment, the enhancement of cytochrome C activity may be achieved by increasing an expression of cytochrome C at a gene (mRNA) level and/or a protein level and/or the activity of the cytochrome C protein per se, but without limitations thereto.

In an embodiment, the enhancement of cytochrome C activity may be achieved by introducing a gene encoding the cytochrome C. As such, the introduction of a cytochrome C-coding gene may increase the L-amino acid production potential that the microorganism retains or generates an L-amino acid production potential that the microorganism lacks.

In an embodiment, the cytochrome C or the gene coding therefor may be derived from a host microorganism (homogenous) or a different microorganism (exogenous). In a specific embodiment, the enhancement of cytochrome C activity may be carried out by introducing an exogenous gene coding for cytochrome C into a host microorganism. The cytochrome C is as described in the foregoing, and for example, may be *Bacillus pseudofirmus* OF4-derived cytochrome C (cytochrome C-551), as represented by the amino acid sequence of SEQ ID NO: 16 (e.g., encoded by cccA (BpOF4_13740)) or the amino acid sequence of SEQ ID NO: 27 (e.g., encoded by cccB (BpOF4_05495)).

In an embodiment, the gene coding for cytochrome C or the L-amino acid producing microorganism having the gene introduced thereinto may comprise a polynucleotide coding for the amino acid sequence of SEQ ID NO: 16, a polynucleotide coding for the amino acid sequence of SEQ ID NO: 27, or a combination thereof. In an embodiment, the L-amino acid producing microorganism may be a microorganism of the genus *Corynebacterium*, for example, *Corynebacterium glutamicum*, which comprises a polynucleotide coding for the amino acid sequence of SEQ ID NO: 16, a polynucleotide coding for the amino acid sequence of SEQ ID NO: 27, or a combination thereof. For example, the L-amino acid producing microorganism may be the microorganism deposited under accession number KCCM12640P.

With respect to a polynucleotide (used interchangeably with "gene") or a polypeptide (used interchangeably with "protein"), as used herein, the wordings "comprising a specific nucleic acid or amino acid sequence", "consisting of a specific nucleic acid or amino acid sequence", and "being expressed as a specific nucleic acid or amino acid sequence" are interchangeable expressions with the equivalent meanings that the polynucleotide or polypeptide essentially comprises the specific nucleic acid or amino acid sequence. Further, these wordings may be construed as "comprising a substantially equivalent sequence" (or as "not excluding introduction of the following mutation"), which results from a mutation (deletion, substitution, modification, and/or addition) to the specific nucleic acid or amino acid sequence insofar as the polynucleotide or polypeptide retains its original function and/or desired function.

In an embodiment, the nucleic acid sequence or amino acid sequence provided herein may comprise mutants thereof obtained by conventional mutation methods, for example, direct evolution and/or site-directed mutagenesis insofar as the mutants retain the original function or desired function of the sequence. In an embodiment, the expression that a polynucleotide or polypeptide "comprises or consists of a specific nucleic acid or amino acid sequence" may mean that a polynucleotide or polypeptide essentially comprises or consists essentially of (i) the specific nucleic acid or amino acid sequence, or (ii) a nucleic acid or amino acid sequence having a sequence identity of 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.5% or greater, or 99.9% or greater (e.g., 60% to 99.5%, 70% to 99.5%, 80% to 99.5%, 85% to 99.5%, 90% to 99.5%, 91% to 99.5%, 92% to 99.5%, 93% to 99.5%, 94% to 99.5%, 95% to 99.5%, 96% to 99.5%, 97% to 99.5%, 98% to 99.5%, or 99% to 99.5%), wherein the polynucleotide or polypeptide retains its original function and/or desired function. As used herein, the term "original function" means the cytochrome C function per se (for amino acid sequence), or a function to coding for a protein having the cytochrome C function (for a nucleic acid sequence) and the term "desired function" means a function to increase an L-amino acid (e.g., L-lysine) production potential in a microorganism or to impart an L-amino acid (e.g., L-lysine) production potential to a microorganism.

For the nucleotide sequences described herein, various modifications can be made in the coding regions insofar as they do not change amino acid sequences and/or functions of the protein (cytochrome C) expressed from the coding regions, due to codon degeneracy or in consideration of the codons preferred by the microorganisms in which the protein are to be expressed.

The term "identity", as used herein, may refer to a degree of identity between given nucleic acid sequences or amino acid sequences, which can be expressed as a percentage (%). For an identity between nucleic acid sequences, the percentage thereof can be determined using, for example, the algorithm BLAST (see Karlin and Altschul, Pro. Natl. Acad. Sci. USA, 90, 5873 (1993)) or FASTA by Pearson (see Methods Enzymol., 183, 63 (1990)). Programs called BLASTN and BLASTX have been developed on the basis of the algorithm BLAST (see http://www.ncbi.nlm.nih.gov).

In an embodiment, a polynucleotide comprising a specific nucleic acid sequence provided herein may be construed to comprise a polynucleotide containing a nucleic acid sequence complementary to the specific nucleic acid sequence as well as a polynucleotide containing the specific nucleic acid sequence or a substantially equivalent nucleic acid sequence thereto. In detail, the complementary polynucleotides can be hybridized at properly adjustable Tm values, for example, at a Tm of 55° C., 60° C., 63° C., or 65° C. according to purposes and can be analyzed in the following condition: such conditions are described in detail in known documents. For example, mentions may be made of a condition in which hybridization is made between genes if their homology is 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 98% or greater, 99.5% or greater, or 99.9% or greater, but not made if their homology is lower than the values or a typical condition for southern hybridization under which one or more, in detail, two or three washes are performed at the temperature and salt concentration of 60° C., 1×SSC (saline-sodium citrate buffer), and 0.1% (w/v) SDS (sodium dodecyl sulfate); 60° C., 0.1×SSC, and 0.1% SDS; or 68° C., 0.1×SSC, and 0.1% SDS, but without limitations thereto. For hybridization, two polynucleotides are required to have complementary sequences to each other. Depending on hybridization stringency, a mismatch or mismatches may be allowed between bases. The term "complementary" may be used to describe a relationship between nucleotide bases that can match up with each other. For DNA, for instance, adenosine is complementary to thymine and cytosine is complementary to guanine. Proper hybridization stringency for polynucleotides may vary, depending on various factors comprising polynucleotide length and complementarity and is well known in the art (see Sambrook et al., 9.50-9.51, 11.7-11.8).

The enhancement of cytochrome C activity may be achieved at a cytochrome C gene (mRNA) level by the following strategies:

1) increasing a copy number of a polynucleotide coding for cytochrome C,
2) modifying an expression regulatory element (sequence) so as to augment the expression of the polynucleotide, or
3) both of 1) and 2), but without limitations thereto.

Strategy 1) of increasing a copy number of a polynucleotide may be carried out by introducing the polynucleotide into a host microorganism via a vector or incorporating the polynucleotide into the chromosome of a host microorganism, without limitations thereto. By way of example, an increased copy number may be achieved by introducing into a host microorganism a polynucleotide encoding exogenous cytochrome C or a variant polynucleotide that is codon-optimized for the polynucleotide. Any exogenous polynucleotide can be used in the present disclosure, without limitations to the origin or sequence thereof as long as the polypeptide encoded thereby exhibits identical or similar activity to cytochrome C. For the introduction, a person skilled in the art could appropriately adopt and/or modify transformation methods known in the art. Once being introduced into a host microorganism, the poly polynucleotide is expressed to generate exogenous cytochrome C.

Strategy 2) of modifying an expression control sequence to promote the expression of a polynucleotide may be applied to both endogenous and exogenous polynucleotides. In order to enhance the expression regulatory activity of the expression regulator sequence, a modification may be made through deletion, addition, conservative or non-conservative substitution of nucleotides, or a combination thereof. Alternatively, the expression control sequence may be replaced by a more potent substituent, but without limitations thereto. The expression control sequence may be at least one selected from the group consisting of a promoter, an operator sequence, a sequence encoding a ribosome binding site, and a sequence for controlling transcriptional and/or translational termination. In an embodiment, a potent exogenous promoter, instead of an endogenous promoter, may be operably linked upstream of a polynucleotide expression unit. Examples of the potent promoter comprise a CJ7 promoter, a lysCP1 promoter, an EF-Tu promoter, a groEL promoter, and an aceA or aceB promoter. More particularly, the potent promoter may be the lysCP1 promoter (WO2009/096689) or the CJ7 promoter (WO2006/065095), both derived from the genus *Corynebacterium*, but is not limited thereto.

Hereinafter, the cases where a gene coding for cytochrome C is introduced into a host microorganism via a vector or incorporated into a chromosome of the microorganism are described in detail. The gene introduction described herein may be performed by i) introducing an exogenous gene (derived from a species heterologous and/or homologous to, but different from the host microorganism) into a host cell via a recombinant vector carrying the gene operably linked thereto or ii) incorporating (e.g., randomly incorporating) the exogenous gene into a chromosome (genome) of a host cell. In the case of ii) incorporation into a chromosome (genome) of a host cell, the incorporation may be made at a site that is irrelevant to the growth of the host cell (e.g., non-transcriptional spacer (NTS), etc.) and/or can increase the efficiency of random incorporation (e.g., retrotransposon, etc.), but without limitations thereto.

For the incorporation of a gene or a vector, a person skilled in the art could appropriately adopt a transformation method known in the art. As used herein, the term "transformation" may refer to an action by which a vector carrying a polynucleotide coding for a target protein (cytochrome C) is introduced into a host microorganism to express the protein encoded by the polynucleotide in the host cell. The introduced polynucleotide may be located inside or outside the chromosome of the host microorganism as long as it is expressed in the host microorganism. In addition, the polynucleotide comprises a DNA or an RNA coding for a target protein. So long as it enables the introduction and expression of the polynucleotide in a host microorganism, any delivery means may be employed. For example, a polynucleotide may take a form of an expression cassette that comprises all the elements necessary for autonomous expression in order that the polynucleotide is introduced into a host cell. The expression cassette may conventionally comprise expression regulatory elements operably linked to the polynucleotide, such as a promoter, a transcription stop signal, a ribosome binding site, and/or a translation stop signal. The expression cassette may be an expression vector that can replicate by itself. In addition, the polynucleotide per se may be introduced into a host cell and may be operably linked to a sequence necessary for expression in the host cell. As used herein, the term "operably linked" means a functional connection between an expression regulatory element (e.g., promoter) and the polynucleotide so that the expression regulatory element can control (e.g., initiate) the transcription of the polynucleotide. An operable linkage can be accomplished using a genetic recombination technology known in the art, for example, typical site-specific DNA cleavage and ligation, but without limitations thereto.

Any introduction method may be employed as long as it allows the transformation of the polynucleotide into a host microorganism. Transformation techniques known in the art could be properly selected according to host microorganisms. Examples of the transformation techniques known in the art may comprise electroporation, calcium phosphate ($CaPO_4$) precipitation, calcium chloride ($CaCl_2$) precipitation, microinjection, polyethylene glycol (PEG)-mediated uptake, DEAE-dextran-mediated delivery, cationic liposome method, lipofection, and lithium acetate-DMSO method, but are not limited thereto.

A person skilled in the art could select a suitable method for incorporating a gene into a genome (chromosome) in a cell. For example, the incorporation may be accomplished using an RNA-guided endonuclease system (for example, at least one selected from the group consisting of a mixture of (a) RNA-guided endonuclease (e.g., Cas9 protein, etc.), a gene coding therefor, or a vector carrying the gene; and (b) guide RNA (i.e., single guide RNA (sgRNA), etc.), DNA coding therefor, or a vector carrying the DNA (e.g., a mixture of RNA-guided endonuclease protein and guide RNA), a complex (e.g., ribonucleoprotein (RNP), and a vector carrying a recombinant vector (e.g., RNA-guided endonuclease encoding gene and a DNA coding for guide RNA, etc.)), but without limitations thereto.

Provided according to another embodiment is a use of a cytochrome C-coding gene, a recombinant vector carrying (comprising) the gene, and/or a cell anchoring (comprising) the recombinant vector in enhancing an L-amino acid production potential in a microorganism and/or in imparting an L-amino acid production potential to a microorganism and/or in preparing a microorganism having L-amino acid production potential.

Another embodiment provides a composition for producing an L-amino acid, the composition comprising a gene coding for cytochrome C, a recombinant vector carrying the gene, or a cell anchoring the recombinant vector.

Another embodiment provides a composition for producing an L-amino acid, the composition comprising a gene coding for cytochrome C, a recombinant vector carrying the gene, or a combination thereof. The composition for producing an L-amino acid may be used to allow a microorganism to produce an L-amino acid, to increase in L-amino acid production potential, and/or to be endowed with an L-amino acid production potential.

Another embodiment provides a method for enhancing an L-amino acid production potential in a microorganism or for imparting an L-amino acid production potential to a microorganism, the method comprising a step of introducing (transforming) a cytochrome C-encoding gene or a recombinant vector carrying the gene into the microorganism.

The cytochrome C, the gene coding therefor, and the microorganism are as described above.

As used herein, the term "vector" may refer to a DNA construct containing a target protein-encoding nucleotide sequence which is operably linked to a suitable control sequence capable of effecting the expression of the target protein in a suitable host. Such control sequences comprise a promoter to effect transcription, an optional operator sequence to control such transcription, a sequence encoding suitable mRNA ribosome binding sites, and/or sequences which control termination of transcription and/or translation. Once transformed into a suitable host, the vector may replicate and function to express the target protein independently of the host genome or may integrate into the genome itself.

So long as it replicates in a host cell, any vector can be employed herein with no particular limitations imparted thereto. It may be selected from among commonly used vectors. Examples of such commonly used vectors may include plasmids, cosmids, viruses, and bacteriophages, which may be in natural or recombinant states. For instance, the phage vector or cosmid vector is exemplified by pWE15, M13, MBL3, MBL4, IXII, ASHII, APII, t10, t11, Charon4A, and Charon21A. The plasmid vectors may be derived from pBR-, pUC-, pBluescriptll-, pGEM™, pTZ-, pCL- and pET lineages. Examples of the vector may include, but are not limited to, pDZ, pACYC177, pACYC184, pCL, pECCG117, pUC19, pBR322, pMW118, and pCC1BAC.

A vector available herein may be a known expression vector and/or a vector for incorporating a polynucleotide into a chromosome of a host cell. The incorporation of a polynucleotide into a chromosome of a host cell may be achieved using any method known in the art, for example, homologous recombination, but with no limitations thereto. The vector may further carry a selection marker for determining whether a gene of interest is incorporated into a chromosome. The selection marker is to select a cell transformed with the vector, that is, to determine the incorporation of the polypeptide and may be selected from among genes that confer selectable phenotypes, such as drug resistance, auxotrophy, cytoxic drug resistance, and expression surface proteins. Under the circumstance where a selective agent is applied to cells, only the cells capable of expressing a selection marker can survive or express a distinctive phenotype so that the transformed cells can be selected.

Another embodiment provides a method for producing an L-amino acid, the method comprising a step of culturing the L-amino acid producing microorganism in a medium. The method may further comprise a step of recovering the I-amino acid from the cultured microorganism, the medium or both thereof, subsequent to the culturing step.

In the method, the step of culturing the microorganism may be performed by known batch culturing methods, continuous culturing methods, fed-batch culturing methods, etc., but with no particular limitation thereto. Here, culture conditions may be maintained at an optimal pH (e.g., a pH of 5 to 9, specifically a pH of 6 to 8, and most specifically a pH of 6.8) using basic compounds (e.g., sodium hydroxide, potassium hydroxide, or ammonia) or acidic compounds (e.g., phosphoric acid or sulfuric acid) or at an aerobic condition by supplying oxygen or oxygen-containing gas mixture to a cell culture, but with no particular limitations thereto. The culture temperature may be maintained at 20 to 45° C. and specifically at 25 to 40° C. and the cells may be cultured for about 10 to 160 hours, but with no limitations thereto. The L-amino acid (i.e., L-lysine) produced by the cultivation may be exported to the culture medium or remain within the cells.

A medium available for the cultivation may comprise at least one selected from sugar and carbohydrate (e.g., glucose, sucrose, lactose, fructose, maltose, molasses, starch, and cellulose), oil and fat (e.g., soybean oil, sunflower seed oil, peanut oil, and coconut oil), fatty acid (e.g., palmitic acid, stearic acid, and linoleic acid), alcohol (e.g., glycerol and ethanol), and organic acid (e.g., acetic acid), as a carbon source; at least one selected from nitrogen-containing organic compounds (e.g., peptone, yeast extract, meat juice, malt extract, corn solution, soybean meal powder, and urea), inorganic compounds (e.g., ammonium sulfate, ammonium chloride, ammonium phosphate, ammonium carbonate, and ammonium nitrate), as a nitrogen source; at least one selected from potassium dihydrogen phosphate, dipotassium phosphate, or sodium-containing salt corresponding thereto, as a phosphorus source; and at least one selected from other essential growth-stimulating substances, such as metal salts (e.g., magnesium sulfate or iron sulfate), amino acids, and/or vitamins, without being limited thereto.

In the step of recovering the L-amino acid (i.e., L-lysine), the desired amino acid may be collected from the medium, the culture, or the microorganisms, using a suitable method known in the art according to the culturing method. By way of example, the recovering step may be carried out using at least one method selected from centrifugation, filtration, anion exchange chromatography, crystallization, and HPLC, and the desired acrylic acid can be recovered from the medium or microorganism using any suitable method known in the art. The method may further comprise a purification step prior to, simultaneously with, or subsequent to the recovering step.

Advantageous Effects

Introduction of an exogenous gene makes a lysine producing strain increase in lysine production activity and retain the increased lysine production activity to the later phase of growth, thereby improving the lysine production potential.

DESCRIPTION OF DRAWINGS

FIG. 1 is a schematic diagram accounting for analysis results of nucleic acid sequences of the library vectors prepared in an embodiment.

MODE FOR INVENTION

Hereinafter, the present disclosure will be described in more detail with examples, but these examples are only for illustrative purpose and are not intended to limit the scope of the disclosure. It is obvious to a person skilled in the art that the examples described below may be modified without departing from the spirit of the disclosure.

Example 1: Construction of Vector Library for Gene Delivery

In order to investigate genes useful for enhancing the lysine production potential of *Corynebacterium glutamicum*, a library of genomic DNAs derived from extremophile bacteria, which adapt to and survive various extreme environments, was constructed. As extremophile bacteria, which can grow under the extreme conditions of high osmotic pressures, high temperatures, hypoxia, and various hydrogen ion concentrations, the four representative microorganisms, *Bacillus atrophaeus* (ATCC 49337), *Bacillus licheniformis* (KCTC 1030), *Lactobacillus fermentum* (KCTC 3112), and *Bacillus pseudofirmus* OF4 (ATCC BAA2126) were used.

First, genomic DNAs were extracted from the four strains, using a QIAamp DNA Micro Kit (QIAGEN). The genomic DNAs thus procured were digested with the restriction enzyme Sau3A1 (NEB) at 37° C. for 10 min and then at 65° C. for 30 min to give incomplete gene fractions which were then run on 1% agarose gel by electrophoresis. Only the gel fraction in the band of 5 to 7 kb were excised. From the gel, the gene fragments for insertion were eluted using GeneAll Expin GEL SV kit (Seoul, KOREA).

The gene fragments thus procured were incubated with the restriction enzyme BamHI-HF (NEB) at 37° C. for one hour and then with CIP (NEB) at 37° C. for 30 min before ligation to the pECCG117 vector (Korean Patent No. 0057684). The resulting recombinant vector was transformed into *E. coli* DH5a which was then spread on an LB plate containing kanamycin (25 mg/l). Genes from a single colony were amplified by PCR using the primers of SEQ ID NOS: 1 and 2 shown in Table 1, below. PCR was started with an initial 10 min denaturing at 95° C. and proceeded with 30 cycles of denaturing at 95° C. for 1 min, annealing at 55° C. for 1 min, and extension at 72° C. for 4 min, followed by final extension at 72° C. for 10 min.

TABLE 1

| Description | sequence (5' -> 3') | SEQ ID NO: |
|---|---|---|
| F primer | TAA TAC GAC TCA CTA TAG GG | 1 |
| R primer | CAA TTA ACC CTC ACT AAA | 2 |

Detection of the PCR products confirmed that extremophile bacterium-derived genomic DNA fragments having a size of 3 to 5 kb were successfully inserted into the pECCG117 vector at a rate of 99% or higher. As many as 10,000 colonies of the transformants were secured per strain. From the transformants, plasmids were extracted using a plasmid prep kit (QIAGEN). The library vectors were called p117-Lib.Bat (derived from *Bacillus atrophaeus*), p117-Lib.Bli (derived from *Bacillus licheniformis*), p117-Lib.Lfe (derived from *Lactobacillus fermentum*), and p117-Lib.Bps (derived from *Bacillus pseudofirmus* OF4).

Example 2: Generation and Screening of Strain Having Vector Library Introduced Thereinto The four library vectors (p117-Lib.Bat, p117-Lib.Bli, p117-Lib.Lfe, and p117-Lib.Bps) constructed in Example 1 were transformed into the lysine producing strain *Corynebacterium glutamicum* KCCM11016P (Korean Patent No. 10-0159812) by an electric pulse method (Van der Rest et al., Appl. Microbiol. Biotecnol. 52:541-545, 1999) and the bacteria was spread on a complex plate medium containing kanamycin (25 mg/l). Finally, about 5,000 colonies per library vector were procured and named LYS_Lib.Bat, LYS_Lib.Bli, LYS_Lib.Lfe, and LYS_Lib.Bps, respectively. The KCCM11016P strain which had been transformed with the pECCG117 vector carrying no gDNA-derived gene fragments was used as a control against the library strains and named LYS_117 control.

The composition of the complex plate medium used was as follows:
<Complex Plate Medium (pH 7.0)>
Glucose 10 g, Peptone 10 g, Beef extract 5 g, Yeast extract 5 g, Brain Heart Infusion 18.5 g, NaCl 2.5 g, Urea 2 g, Sorbitol 91 g, Agar 20 g (per liter of distilled water)

The four KCCM11016P-based library strains procured were each inoculated into 96-Deep Well Plate-Dome (Bioneer) containing 400 μl of a screening medium, using the colony-picker (SINGER, PIXL) and incubated in a plate shaking incubator (TAITEC) at 32° C. for 15 hr while shaking at 12,000 rpm.

The seed medium has the following composition:
<Screening Medium (pH 7.0)>
Glucose 45 g, Sugar beet-derived molasses 10 g, Soybean steep liquid 10 g, $(NH_4)_2SO_4$ 24 g, $MgSO_4 \cdot 7H_2O$ 0.6 g, $KH_2PO_4$ 0.55 g, Urea 5.5 g, Biotin 0.9 mg, Thiamine HCl 4.5 mg, Calcium pantothenate 4.5 mg, Nicotinamide 30 mg, $MnSO_4 \cdot 5H_2O$ 9 mg, $ZnSO_4 \cdot 5H_2O$ 0.45 mg, $CuSO_4 \cdot 5H_2O$ 0.45 mg, $FeSO_4 \cdot 5H_2O$ 9 mg, and Kanamycin 25 mg (per liter of distilled water)

While being cultured, the cells were monitored for growth with the aid of a microplate-reader (BioTek). Concentrations of glucose and produced lysine in the media were measured using a sugar analyzer and (YSI) and a HPLC instrument (Shimadzu), respectively.

Through the experiment, final selection was made of three strains that exhibits excellent growth and high glucose consumption rates, compared to the control (Table 2). The three selected strains were found to anchor the LYS_Lib.Bps library vectors thereat. Although being similar to the control to LYS_117 control in terms of yield and OD value, these strains were found excellent in productivity because their glucose consumption rates per hour (g/hr) in sampling point sections were increased by 118% relative to 100% of LYS_117 control.

TABLE 2

| Strain | OD 600 | | Relative Sugar Consumption Rate (%) | 36-Hr Lysine Yield (%) |
|---|---|---|---|---|
| | 12 hr | 36 hr | | |
| LYS_117 control | 17.1 | 62.7 | 100 | 15.8 |
| LYS_Lib.Bps #257 | 17.4 | 63.5 | 117.4 | 15.9 |
| LYS_Lib.Bps #881 | 16.8 | 64.1 | 111.1 | 15.6 |
| LYS_Lib.Bps #4213 | 18.1 | 63.8 | 118.0 | 15.8 |

Example 3: Base Sequencing of gDNA Library

To identify sequences of the genes introduced into the three colonies selected in Example 2, LYS_Lib.Bps #257, #881, and #4213, gDNA library gene fragments that the colonies contained were amplified by PCT using the primers of SEQ ID NOS: 1 and 2 shown in Table 1 of Example 1. PCR was performed in the same condition as in Example 1. The PCR fragments were isolated using the GeneAll Expin GEL SV kit (Seoul, KOREA) and analyzed for base sequences. Based on the analysis results, gene information was obtained by BLAST (NCBI reference sequence NC_013791.2).

The analysis results are depicted in FIG. 1. As shown in FIG. 1, the base sequencing result informed that there are a 4794-bp gene fragment in the colony LYS_Lib.Bps #257, a 3985-bp gene fragment in the colony #881, and a 4483-bp fragment in the colony #4213. The three colonies were found to have BpOF4_13735 and BpOF4_13740 as intact gene ORFs in common with one another. Subsequently, additional experiments were performed for influences of the two genes.

Example 4: Construction of Vector and Strain Having Individual Gene Introduced Thereinto For use in investing influences of the two individual genes identified in Example 3, a genomic insertion vector was constructed. For use as a base vector for gene insertion, first, pDZ_Δ2284 vector targeting Ncgl2284, which is one of transposases, was constructed.

In detail, ATCC13032 gDNA was used as a DNA template for PCR. Primers were prepared with reference to the NCBI base sequence (NC_003450.3). In the presence the primers of SEQ ID NOS: 3 and 4, PCR was started with 10 min denaturing at 95° C. and proceeded with 30 cycles of denaturing at 95° C. for 1 min, annealing at 55° C. for 1 min, and extension at 72° C. for 4 min, followed by final extension at 72° C. for 10 min to afford a 5' DNA fragment about 900 bp long. Likely, PCR was conducted using primers of SEQ ID NOS: 5 and 6 in the same condition as in the foregoing to amplify a 3' DNA fragment. The two DNA amplicons were purified using GeneAll Expin GEL SV kit (Seoul, KOREA) and digested with the restriction enzyme XbaI (NEB). Using an infusion cloning kit, the digest was ligated to pDZ (Korean Patent No. 2009-0094433) that has been thermally treated at 65° C. for 20 min. The recombinant plasmid thus formed was transformed into E. coli DH5α which was then spread on an LB plate medium containing kanamycin (25 mg/l). The gene inserted into pDZ vector was subjected to base sequencing to finally prepare pDZ_Δ2284 vector.

An additional enrichment (expression) vector for individual genes was constructed by digesting the base vector pDZ_Δ2284 with the restriction enzymes NdeI and CIP (NEB), thermally treating the digested vector at 65° C. for 20 min, purifying the thermally treated vector, and ligating a promoter and each gene DNA fragment to the vector with the aid of an Infusion Cloning Kit. As the promoter for the additional gene expression, the gapA gene promoter of SEQ ID NO: 13 was employed. In order to obtain the promoter, PCR was performed using primers of SEQ ID NOS: 7 and 8, with ATCC13032 gDNA (NC_003450.3) serving as a template. In the presence of pfu polymerase, PCR was started with 10 min denaturing at 95° C. and proceeded with 30 cycles of denaturing at 95° C. for 1 min, annealing at 55° C. for 1 min, and extension at 72° C. for 1 min, followed by final extension at 72° C. for 10 min. DNA fragments for the two genes BpOF4_13735 and BPOF4_13740 were amplified from Bacillus pseudofirmus OF4 gDNA in the same manner as for the promoter, with the exception of using the primers of SEQ ID NOS: 9 and 10 for BpOF4_13735 (SEQ ID NO: 14) and the primers of SEQ ID NO: 11 and 12 for BpOF4_13740 (SEQ ID NO: 15). The DNA fragments thus obtained were purified using GeneAll Expin GEL SV kit (Seoul, KOREA) and then ligated to pDZ_Δ2284 to finally afford two different vectors: pDZ_Δ2284::PgapA BpOF4_13735 and pDZ_Δ2284::PgapA BpOF4_13740.

The two vector constructs were each transformed into the lysine producing strain Corynebacterium glutamicum KCCM11016P (Korean Patent No. 10-0159812), using an electric pulse method. Secondary DNA-crossover enriched the individual genes in the strains. The two final strains thus constructed were named KCCM11016P_Δ2284::PgapA BpOF4_13735 and KCCM11016P_Δ2284::PgapA BpOF4_13740, respectively.

The primers, promoters, nucleic acid sequences of BpOF4 genes, and amino acid sequences encoded by the genes used herein are summarized in Table 3, below:

TABLE 3

| Description | Sequence (5' → 3' or N → C) | SEQ ID NO |
|---|---|---|
| F primer for ATCC13032 gDNA | GTACCCGGGGATCCTCTAGAATCGCAATGATAGCCCATTC | 3 |
| R primer for ATCC13032 gDNA | TTGGTCAAACCTCCCCTcatatgCAGAAATCCACATCAAT | 4 |
| F primer for ATCC13032 gDNA | ATTGATGTGGATTTCTGcatatgAGGGGAGGTTTGACCAA | 5 |
| R primer for ATCC13032 gDNA | GCCTGCAGGTCGACTCTAGAATGCATCTCTGGATGATGTG | 6 |
| F primer for gapA promoter | ATTGATGTGGATTTCTGcatAAGCCTAAAAACGACCGAGC | 7 |
| R primer for gapA promoter | GTTGTGTCTCCTCTAAAGATTGTAG | 8 |
| F primer for BpOF4_13735 | ATCTTTAGAGGAGACACAACATGGATGAAAAAAGAAAAGC | 9 |
| R primer for BpOF4_13735 | TTGGTCAAACCTCCCCTcatTTAACGCCCCAGCCAAAAATTCC | 10 |
| F primer for BpOF4_13740 | ATCTTTAGAGGAGACACAACATGAAAGGAAGACCACTTTT | 11 |
| R primer for BpOF4_13740 | TTGGTCAAACCTCCCCTcatTTATTCTGAAATAGATAGTA | 12 |

TABLE 3-continued

| Description | Sequence (5' → 3' or N → C) | SEQ ID NO |
|---|---|---|
| gapA promoter | AAGCCTAAAAACGACCGAGCCTATTGGGATTACCATTGAAGCCA GTGTGAGTTGCATCACATTGGCTTCAAATCTGAGACTTTAATTT GTGGATTCACGGGGGTGTAATGTAGTTCATAATTAACCCCATTC GGGGGAGCAGATCGTAGTGCGAACGATTTCAGGTTCGTTCCCTG CAAAAACTATTTAGCGCAAGTGTTGGAAATGCCCCCGTTTGGGG TCAATGTCCATTTTTGAATGTGTCTGTATGATTTTGCATCTGCT GCGAAATCTTTGTTTCCCCGCTAAAGTTGAGGACAGGTTGACAC GGAGTTGACTCGACGAATTATCCAATGTGAGTAGGTTTGGTGCG TGAGTTGGAAAAATTCGCCATACTCGCCCTTGGGTTCTGTCAGC TCAAGAATTCTTGAGTGACCGATGCTCTGATTGACCTAACTGCT TGACACATTGCATTTCCTACAATCTTTAGAGGAGACACAAC | 13 |
| BpOF4_13735 nucleic acid sequence | ATGGATGAAAAAAGAAAAGCGATTATTATAAATGAAATTAAGTA CTGGCGCGAATCAAAGCTGCTTCCCTCCCAGTATTGTGATTTCT TATTAACGCTTTATTCAGAAGGAGAGGACCTAGAGACAGCCGAC TCAGGAAAGCGCTTCCGAAACATTCGGACAATCTATTCGTTTAT TATTGTTCAGCTTTCATTTGTCTTTACTGCTCTTGTCATTTATT TTACTGATTTTTCAAATGGATTGCAAATGCTTATTGGTTTGACT TTTTCGATTATTGTGTTAATTATAGCAAAACGGACTAGGGCAGA TGCCTTTTTTCTTAAACAATTTTACTATTTTATAGGGGCTCTGA TCCTCTTTTTACTAACGATTGAATGGGTTGTTCACTACAAAAGT ACTAATAACCTTTTATTATCAGCAACAATCATTTTACATTGCGT TTTTTGGCTCTTTGCAGGGCTGAAATGGAAAATGCGATTTTTTA CGATATCTGCTATACTAGGACTAGTAGTGTTAGGAATTTTTTG GCTGGGGCGTTAA | 14 |
| BpOF4_13740 nucleic acid sequence | ATGAAAGGAAGACCACTTTTACCATTTGCGATCATAGCAATTGT CGGGATTGTTGTTATGATTTCGCTTTCATTTATTGGGTTAAACC AGCGTGAAGCGATGCAGGCAGATGAAGAAGGAGAAGAAGAAGTA ACTGAAATTGAAGATCCGGTAGCAGCTGGAGAAGAATTAGTGCA AACTTCTTGTATCGGTTGTCACGGTGGCGATTTAAGCGGTGGTG CAGGTCCTGCCCTAACGTCTCTTGAAGGTCAATACACTCAAGAA GAAATTACAGATATTGTTGTTAATGGGATTGGATCAATGCCGTC AGTTAACGATAACGAAGTAGAAGCAGACGCAATTGCACAGTATT TACTATCTATTTCAGAATAA | 15 |
| BpOF4_13740 amino acid sequence | MKGRPLLPFAIIAIVGIVVMISLSFIGLNQREAMQADEEGEEEV TEIEDPVAAGEELVQTSCIGCHGGDLSGGAGPALTSLEGQYTQE EITDIVVNGIGSMPSVNDNEVEADAIAQYLLSISE* | 16 |

Example 5: Assay for Lysine Production Potential of Strains Anchoring Individual Genes Thereat The two strains prepared in Example 4 were cultured in the following manner so as to measure OD values, lysine production yields, and sugar consumption rates (g/hr). First, each strain was inoculated in a 250-ml corner-baffle flask containing 25 ml of a seed medium and then cultured at 30° C. for 20 hours while shaking at 150 rpm. Thereafter, 1 ml of the seed culture was inoculated into a 250 ml corner-baffle flask containing 24 ml of a production medium and then cultured at 32° C. for 40 hours while shaking at 150 rpm. Compositions of the seed medium and the production medium were as follow, and the culture results are given in Table 4, below.

<Seed Medium (pH 7.0)>
Glucose 20 g, Peptone 10 g, Yeast extract 5 g, Urea 1.5 g, $KH_2PO_4$ 4 g, $K_2HPO_4$ 8 g, $MgSO_4 \cdot 7H_2O$ 0.5 g, Biotin 100 μg, Thiamine HCl 1,000 μg, Calcium pantothenate 2,000 μg, Nicotinamide 2000 μg (per liter of distilled water)

<Production Medium (pH 7.0)>
Glucose 45 g, Sugar beet-derived molasses 10 g, Soybean steep liquid 10 g, $(NH_4)_2SO_4$ 24 g, $MgSO_4 \cdot 7H_2O$ 0.6 g, $KH_2PO_4$ 0.55 g, Urea 5.5 g, $CaCO_3$ 30 g, Biotin 0.9 mg, Thiamine HCl 4.5 mg, Calcium pantothenate 4.5 mg, Nicotinamide 30 mg, $MnSO_4 \cdot 5H_2O$ 9 mg, $ZnSO_4 \cdot 5H_2O$ 0.45 mg, $CuSO_4 \cdot 5H_2O$ 0.45 mg, $FeSO_4 \cdot 5H_2O$ 9 mg, and Kanamycin 25 mg (per liter of distilled water)

TABLE 4

OD Values, Lysine Production Potential, and Sugar Consumption Rate of Individual Gene-Enhanced Strain

| Strain | OD FN | Relative Sugar Consumption Rate (%) | FN (final) Lysine Production Yield (%) |
|---|---|---|---|
| KCCM11016P | 68.5 | 99.5 | 18.9 |
| KCCM11016P_Δ2284 | 67.8 | 100 | 18.7 |
| KCCM11016P_Δ2284::PgapA BpOF4_13735 | 68.3 | 103 | 18.8 |
| KCCM11016P_Δ2284::PgapA BpOF4_13740 | 69.1 | 131.5 | 18.6 |

The strain in which BpOF4_13735, which is one of the two genes procured from the gDNA library, was overexpressed did not exhibit a significantly improved effect in terms of lysine production yield and sugar consumption rate, compared to the parent strain KCCM11016P_Δ2284. In contrast, the KCCM11016P_Δ62284::PgapA BpOF4_13740 strain, although similar to the parent strain KCCM11016P_Δ62284 in the final OD and yield, was found to increase in sugar consumption rate per hour over the middle culturing section (17 to 24 hours) by 31.5% compared to the parent strain.

Finally, it was found that the effects of the colonies LYS_Lib.Bps #257, #881, and #4213 revealed in Example 2 were attributed to the enhancement of BpOF4_13740.

Example 6: Enhancement of Lysine Production Potential in BpOF4_13740-Enhanced Strain In order to secondarily verify the effect of BpOF4_13740 gene confirmed in Example 5, BpOF4_13740 gene was assayed after being enhanced with a different promoter. And the effect was also assayed for the BpOF4_05495 gene further confirmed by NCBI BLAST analysis as same functional protein.

To this end, a gene expression vector was additionally constructed in the same manner as for the vector constructed in Example 3.

A sigB promoter was amplified by PCR using the primers of SEQ ID NOS: 17 and 18, with ATCC13032 gDNA serving as a template. Using the primers of SEQ ID NOS: 19 and 12, PCR was performed on the template of *Bacillus pseudofirmus* OF4 gDNA to amplify BpOF4_13740 gene. These two gene fragments were ligated to pDZ_Δ2284 to construct pDZ_Δ2284::PsigB BpOF4_13740 vector.

Enhancement of the BpOF4_05495 gene was also achieved in the same manner to construct pDZ_Δ2284::PsigB BpOF4_05495 and pDZ_Δ2284::PgapA BpOF4_05495 vectors. A BpOF4_05495 gene fragment was procured using the primers of SEQ ID NOS: 20 and 21 and the primers of SEQ ID NOS: 22 and 21. An effect obtained upon simultaneous enrichment of the two genes was also examined. In this regard, primers of SEQ ID NOS: 23 and 24, which were designed to contain a ribosome-binding sequence (RBS), were additionally synthesized to construct pDZ_Δ2284::PsigB BpOF4_13740_05495 and pDZ_Δ2284::PgapA BpOF4_13740_05495 vectors.

The five additional vector constructs (pDZ_Δ2284::PsigB BpOF4_13740 vector, pDZ_ΔA2284::PsigB BpOF4_05495 vector, pDZ_Δ2284::PgapA BpOF4_05495 vector, pDZ_Δ2284::PsigB BpOF4_13740_05495 vector, and pDZ_Δ2284::PgapA BpOF4_13740_05495 vector) were each transformed into the lysine producing strain *Corynebacterium glutamicum* KCCM11016P (Korean Patent No. 10-0159812) by an electric pulse method and subjected to secondary DNA-crossover to prepare strains having the individual genes enhanced therein.

The five strains thus obtained were named KCCM11016P_Δ2284::PsigB BpOF4_13740, KCCM11016P_Δ2284::PsigB BpOF4_05495, KCCM11016P_Δ2284::PgapA BpOF4_05495, KCCM11016P_Δ2284::PsigB BpOF4_13740_05495, and KCCM11016P_Δ2284::PgapA BpOF4_13740_05495, respectively.

The primers, promoters, nucleic acid sequences of BpOF4_05495, and amino acid sequence encoded by the gene used herein are summarized in Table 5, below:

TABLE 4

| Description | sequence (5' → 3' or N → C) | SEQ ID NO |
|---|---|---|
| F primer for sigB promoter | ATTGATGTGGATTTCTGcatTGCAGCACCTGGTGAGGTGG | 17 |
| R primer for sigB promoter | AACTGGCCTCCTAAATTCGCGGTTC | 18 |
| F primer for BPOF4_13740 | GCGAATTTAGGAGGCCAGTTATGAAAGGAAGACCACTTTT | 19 |
| F primer for BpOF4_05495 | GCGAATTTAGGAGGCCAGTTATGAAAAAGTTTTTATTAGC | 20 |
| R primer for BpOF4_05495 | TTGGTCAAACCTCCCCTcatTTATTGAGCTTCAAGCCATG | 21 |
| F primer for BpOF4_05495 | ATCTTTAGAGGAGACACAACATGAAAAAGTTTTTATTAGC | 22 |
| R primer for RBS insertion | CTGTGTTTCCTCCTTTCTCCTGTTATTCTGAAATAGATAGTA | 23 |
| F primer for RBS insertion | CAGGAGAAAGGAGGAAACACAGATGAAAAAGTTTTTATTAGC | 24 |
| sigB promoter | TGCAGCACCTGGTGAGGTGGCTGAGCCGGTGATTGAAAAGATTGCAC AAGGTTTACGTGAGCGCGGAATCACCGTGGAACAAGGACGATTCGGC GCAATGATGAAGGTCACATCGGTTAACGAAGGCCCCTTCACCGTTTT GGTCGAGTGCTAGCCAGTCAATCCTAAGAGCTTGAAACGCCCCAATG TGGGGGTGTTAAGAACTCCATAAAAGCGCTTGGGAACTTTTTGTGGA AGCAGTCCGTTGAACCTCTTGAACCGCGAATTTAGGAGGCCAGTT | 25 |
| BPOF4_05495 nucleic acid sequence | ATGAAAAAGTTTTTATTAGCTCTTGGCGCAGTTGTTGCTCTTACAGC ATGTGGCGGCGGAGACGAAGCTGCTCCACCGGTTGATGAGGAGTCTC CAGCAGTAGATGAAGCTCCAGCAGATGAGCCTGCAGATGATGCAACA GCTGGTGATTACGATGCAGAATCAGCTCGTGCTACATATGAGCAAAG CTGTATCGCATGTCATGGCGGCGATCTTCAAGGGGCATCAGGTCCAG CTCTAGTAGGAACTGGCCTGTCAGCTGCTGAAATTCAAGACATCATC CAAAACGGACAAGGTTCAATGCCTGCTCAAAATTTAGATGATGACGA AGCTGCTAACCTAGCTGCATGGCTTGAAGCTCAATAA | 26 |
| BPOF4_05495 amino acid sequence | MKKFLLALGAVVALTACGGGDEAPPVDEESPAVDEAPADEPADDATA GDYDAESARATYEQSCIACHGGDLQGASGPALVGTGLSAAEIQDIIQ NGQGSMPAQNLDDDEAANLAAWLEAQ | 27 |

The five strains, KCCM11016P_Δ62284::PsigB BpOF4_13740, KCCM11016P_Δ2284::PsigB BpOF4_05495, KCCM11016P_Δ2284::PgapA BpOF4_05495, KCCM11016P_Δ2284::PsigB BpOF4_13740_05495, and KCCM11016P_Δ2284::PgapA BpOF4_13740_05495, were evaluated in flasks in the same condition as in Example 5 and the results are given in Table 6, below.

TABLE 6

OD Values, Lysine Production Potentials, and Sugar Consumption Rates in Strains Enhanced with Genes Individually or in Combination

| Strain | OD FN | FN Lysine Conc. (g/L) | FN Lysine Yield % | Relative Sugar Consumption Rate (%) |
|---|---|---|---|---|
| KCCM11016P | 68.4 | 9.0 | 18.4 | 101.6 |
| KCCM11016P_Δ2284 | 68.1 | 8.7 | 18.7 | 100 |
| KCCM11016P_Δ2284::PsigB BpOF4_13740 | 67.5 | 8.4 | 18.1 | 107.1 |
| KCCM11016P_Δ2284::PgapA BpOF4_13740 | 68.8 | 9.2 | 18.4 | 142.1 |
| KCCM11016P_Δ2284::PsigB BpOF4_05495 | 68.8 | 8.7 | 18.2 | 120.2 |
| KCCM11016P_Δ2284::PgapA BpOF4_05495 | 68.9 | 8.9 | 17.8 | 136.6 |
| KCCM11016P_Δ2284::PsigB BpOF4_13740_05495 | 68.4 | 9.3 | 19.3 | 114.8 |
| KCCM11016P_Δ2284::PgapA BpOF4_13740_05495 | 69 | 9.5 | 19.0 | 145.9 |

Expression of BpOF4_13740 gene under the control of sigB promoter and gapA promoter resulted in increasing sugar consumption rates per hour by 7.1% and 42.1%, respectively, compared to the control KCCM11016P_Δ2284. In addition, when BpOF4_05495 gene, which encodes a similar protein, was additionally introduced under the control of sigB and gapA promoters, the sugar consumption rates increased by 20.2% and 36.6%, respectively. The two results indicate that sugar consumption rates (g/hr) increase with the enhancement of the gene under the control of a promoter. In addition, the sugar consumption rate was observed to peak upon simultaneous expression of the genes BpOF4_13740 and BpOF4_05495. In detail, the strain KCCM11016P_Δ2284::PgapA BpOF4_13740_05495 exhibited a sugar consumption rate per hour increased by 45.9%, compared to the control KCCM11016P_Δ2284.

The strain KCCM11016P_Δ2284::PgapA BpOF4_13740_05495 (called as *Corynebacterium glutamicum* CM03-885), which has an enhanced lysine production potential, was deposited in the Korean Culture Center of Microorganisms located in Hongje-dong, Seodamun-Gu, Seoul, Korea on Dec. 13, 2019 and given the accession number KCCM 12640P.

Example 7: Assay for Lysine Production Potential of BpOF4_13740_05495-Enhance Strain

*Corynebacterium glutamicum* KCCM10770P (Korean Patent No. 10-0924065) and KCCM11347P (Korean Patent No. 10-0073610), both of which produce L-lysine, were each enhanced with the genes selected in Example 6. To this end, the genes were introduced in the same manner as in Example 6. Finally, the three vectors pDZ_Δ2284, pDZ_Δ2284::PsigB BpOF4_13740_05495, and pDZ_Δ2284::PgapA BpOF4_13740_05495 were each transformed into the two strains *Corynebacterium glutamicum* KCCM10770P and KCCM11347P to prepare a total of six strains KCCM10770P_Δ2284, KCCM10770P_Δ2284::PsigB BpOF4_13740_05495, KCCM10770P_Δ2284::PgapA BpOF4_13740_05495, KCCM11347P_Δ2284, KCCM11347P_Δ2284::PsigB BpOF4_13740_05495, and KCCM11347P_Δ2284::PgapA BpOF4_13740_05495.

The gene-enhanced strains thus obtained were cultured in the same manner as in Example 5 and measured for OD, lysine production yield, and relative sugar consumption rate per hour (when the sugar consumption rates per hour of KCCM10770P_Δ2284 and KCCM11347P_Δ2284 were set 100%), and the results are given in Table 7, below.

TABLE 7

OD Values, lysine production potential, and Relative Sugar Consumption Rate of Gene-Enhanced Strain

| Strain | OD FN | FN Lysine Conc. (g/L) | FN Lysine Yield % | Relative Sugar Consumption Rate (%) |
|---|---|---|---|---|
| KCCM10770P | 95.5 | 6.7 | 13.3 | 99.4 |
| KCCM10770P_Δ2284 | 95.3 | 6.5 | 13.0 | 100 |
| KCCM10770P_Δ2284::PsigB BpOF4_13740_05495 | 95.0 | 6.5 | 13.0 | 102.5 |
| KCCM10770P_Δ2284::PgapA BpOF4_13740_05495 | 95.9 | 6.3 | 12.7 | 105.6 |
| KCCM11347P | 65.0 | 15.1 | 30.2 | 99.4 |
| KCCM11347P_Δ2284 | 64.7 | 15.3 | 30.6 | 100 |
| KCCM11347P_Δ2284::PsigB BpOF4_13740_05495 | 65.5 | 15.1 | 30.2 | 103.5 |
| KCCM11347P_Δ2284::PgapA BpOF4_13740_05495 | 65.2 | 15.5 | 31.0 | 108.2 |

As shown in Table 7, although similar to the control in terms of OD, FN lysine concentration, and lysine production yield, the gene-enhanced strains prepared in this Example were fermented within a shorter time due to the improved sugar consumption rate thereof.

Example 8: Preparation of BpOF4_13740_05495-Introduced CJ3P Strain and Assay for Lysine Production Potential Thereof An examination was made to see whether different *Corynebacterium glutamicum* variants producing L-lysine exhibited the same effect as in the foregoing. In this regard, *Corynebacterium glutamicum* CJ3P (Binder et al. Genome Biology 2012, 13:R40), which is made to have an L-lysine production potential by introducing three mutations [pyc (P458S), hom(V59A), and lysC(T311I)] to the wild-type, was enhance with BpOF4_13740_05495 in the same manner as in Example 7. The enhanced strains thus obtained were named CJ3_Δ2284, CJ3_Δ2284::PsigB BpOF4_13740_05495, and CJ3_Δ2284::PgapA BpOF4_13740_05495, respectively. The control CJ3P strain (not enhanced with BpOF4_13740_05495) and the three prepared strains were cultured in the same manner as in Example 5 and measured for OD, lysine production yield, and relative sugar consumption rate per hour (when the sugar consumption rate per hour in each of KCCM10770P_Δ2284 and KCCM11347P_Δ2284 was set 100%), and the results are given in Table 8, below:

TABLE 8

OD Values, Lysine Production Potential, and Relative Sugar Consumption Rate in Gene-Enhanced Strains

| Strain | OD FN | FN Lysine Conc. (g/L) | FN Lysine Yield % | Relative Sugar Consumption Rate (%) |
|---|---|---|---|---|
| CJ3 | 70.5 | 4.5 | 9.0 | 100.4 |
| CJ3_Δ2284 | 71.4 | 4.2 | 8.4 | 100 |
| CJ3_Δ2284::PsigB BpOF4_13740_05495 | 70.9 | 4.4 | 8.8 | 102.9 |
| CJ3_Δ2284::PgapA BpOF4_13740_05495 | 71.6 | 4.6 | 9.2 | 160.9 |

As shown in Table 8, the BpOF4_13740_05495-enhanced strain, although similar to the control in terms of OD, FN lysine concentration, and lysine production yield, was found to increase in sugar consumption rate per hour by 60% or more.

From the above description, it will be understood by those skilled in the art that the present disclosure may be embodied in other specific forms without departing from the spirit or essential characteristics thereof. In this regard, it should be understood that the embodiments described above are illustrative in all aspects and not restrictive. The scope of the present application is to be interpreted as being within the scope of the present application, all changes or modifications derived from the meaning and scope of the appended claims and from their equivalents rather than the detailed description.

The invention claimed is:

1. An L-amino acid producing microorganism having enhanced activity of cytochrome C, wherein the cytochrome C is cytochrome C-551 derived from *Bacillus pseudofirmus* OF4,
   wherein the cytochrome C-551 comprises a polypeptide comprising the amino acid sequence of SEQ ID NO: 16, and a polypeptide comprising the amino acid sequence of SEQ ID NO: 27, and
   wherein the L-amino acid producing microorganism is the genus of *Corynebacterium*.

2. The L-amino acid producing microorganism of claim 1, having an increased sugar consumption rate, compared to a homogeneous microorganism in which the activity of cytochrome C is not enhanced.

3. The L-amino acid producing microorganism of claim 1, having an improved L-amino acid production potential, compared to a homogeneous microorganism in which the activity of cytochrome C is not enhanced.

4. The L-amino acid producing microorganism of claim 3, wherein the L-amino acid is L-lysine.

5. A method for producing an L-amino acid, the method comprising the steps of:
   culturing the L-amino acid producing microorganism of claim 1 in a medium; and
   recovering the L-amino acid from the cultured microorganism, the medium, or both of them.

6. The method of claim 5, wherein the L-amino acid is L-lysine.

* * * * *

SEQUENCE LISTING

```
<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Synthetic_F primer

<400> SEQUENCE: 1
taatacgact cactataggg                                                   20

<210> SEQ ID NO 2
<211> LENGTH: 18
<212> TYPE: DNA
<213> ORGANISM: Artificial Sequence
<220> FEATURE:
<223> OTHER INFORMATION: Synthetic_R primer

<400> SEQUENCE: 2
caattaaccc tcactaaa                                                     18

<210> SEQ ID NO 3
<211> LENGTH: 40
<212> TYPE: DNA
<213> ORGANISM: Artificial Sequence
<220> FEATURE:
<223> OTHER INFORMATION: Synthetic_F primer for ATCC13032 gDNA

<400> SEQUENCE: 3
gtacccgggg atcctctaga atcgcaatga tagcccattc                             40

<210> SEQ ID NO 4
<211> LENGTH: 40
<212> TYPE: DNA
<213> ORGANISM: Artificial Sequence
<220> FEATURE:
<223> OTHER INFORMATION: Synthetic_R primer for ATCC13032 gDNA

<400> SEQUENCE: 4
ttggtcaaac ctcccctcat atgcagaaat ccacatcaat                             40

<210> SEQ ID NO 5
<211> LENGTH: 40
<212> TYPE: DNA
<213> ORGANISM: Artificial Sequence
<220> FEATURE:
<223> OTHER INFORMATION: Synthetic_F primer for ATCC13032 gDNA

<400> SEQUENCE: 5
```

-continued

```
attgatgtgg atttctgcat atgaggggag gtttgaccaa                              40

<210> SEQ ID NO 6
<211> LENGTH: 40
<212> TYPE: DNA
<213> ORGANISM: Artificial Sequence
<220> FEATURE:
<223> OTHER INFORMATION: Synthetic_R primer for ATCC13032 gDNA

<400> SEQUENCE: 6
gcctgcaggt cgactctaga atgcatctct ggatgatgtg                              40

<210> SEQ ID NO 7
<211> LENGTH: 40
<212> TYPE: DNA
<213> ORGANISM: Artificial Sequence
<220> FEATURE:
<223> OTHER INFORMATION: Synthetic_F primer for gapA promoter

<400> SEQUENCE: 7
attgatgtgg atttctgcat aagcctaaaa acgaccgagc                              40

<210> SEQ ID NO 8
<211> LENGTH: 25
<212> TYPE: DNA
<213> ORGANISM: Artificial Sequence
<220> FEATURE:
<223> OTHER INFORMATION: Synthetic_R primer for gapA promoter

<400> SEQUENCE: 8
gttgtgtctc ctctaaagat tgtag                                              25

<210> SEQ ID NO 9
<211> LENGTH: 40
<212> TYPE: DNA
<213> ORGANISM: Artificial Sequence
<220> FEATURE:
<223> OTHER INFORMATION: Synthetic_F primer for BpOF4_13735

<400> SEQUENCE: 9
atctttagag gagacacaac atggatgaaa aagaaaagc                               40

<210> SEQ ID NO 10
<211> LENGTH: 44
<212> TYPE: DNA
<213> ORGANISM: Artificial Sequence
<220> FEATURE:
<223> OTHER INFORMATION: Synthetic_R primer for BpOF4_13735

<400> SEQUENCE: 10
ttggtcaaac ctcccctcat ttaacgcccc agccaaaaaa ttcc                         44

<210> SEQ ID NO 11
<211> LENGTH: 40
<212> TYPE: DNA
<213> ORGANISM: Artificial Sequence
<220> FEATURE:
<223> OTHER INFORMATION: Synthetic_F primer for BpOF4_13740

<400> SEQUENCE: 11
atctttagag gagacacaac atgaaaggaa gaccactttt                              40

<210> SEQ ID NO 12
<211> LENGTH: 40
<212> TYPE: DNA
```

```
<213> ORGANISM: Artificial Sequence
<220> FEATURE:
<223> OTHER INFORMATION: Synthetic_R primer for BpOF4_13740

<400> SEQUENCE: 12
ttggtcaaac ctccctcat ttattctgaa atagatagta                          40

<210> SEQ ID NO 13
<211> LENGTH: 481
<212> TYPE: DNA
<213> ORGANISM: Artificial Sequence
<220> FEATURE:
<223> OTHER INFORMATION: Synthetic_gapA promoter

<400> SEQUENCE: 13
aagcctaaaa acgaccgagc ctattgggat taccattgaa gccagtgtga gttgcatcac    60
attggcttca aatctgagac tttaatttgt ggattcacgg gggtgtaatg tagttcataa   120
ttaaccccat tcgggggagc agatcgtagt gcgaacgatt tcaggttcgt tccctgcaaa   180
aactatttag cgcaagtgtt ggaaatgccc ccgtttgggg tcaatgtcca tttttgaatg   240
tgtctgtatg attttgcatc tgctgcgaaa tctttgtttc cccgctaaag ttgaggacag   300
gttgacacga agttgactcg acgaattatc caatgtgagt aggtttggtg cgtgagttgg   360
aaaaattcgc catactcgcc cttgggttct gtcagctcaa gaattcttga gtgaccgatg   420
ctctgattga cctaactgct tgacacattg catttcctac aatctttaga ggagacacaa   480
c                                                                  481

<210> SEQ ID NO 14
<211> LENGTH: 540
<212> TYPE: DNA
<213> ORGANISM: Artificial Sequence
<220> FEATURE:
<223> OTHER INFORMATION: Synthetic_BpOF4_13735 nucleic acid sequence

<400> SEQUENCE: 14
atggatgaaa aagaaaagc gattattata aatgaaatta agtactggcg cgaatcaaag    60
ctgcttccct cccagtattg tgatttctta ttaacgcttt attcagaagg agaggaccta   120
gagacagccg actcaggaaa gcgcttccga acattcggaa caatctattc gtttattatt   180
gttcagcttt catttgtctt tactgctctt gtcatttatt ttactgattt ttcaaatgga   240
ttgcaaatgc ttattggttt gacttttcg attattgtgt taattatagc aaaacggact   300
agggcagatg ccttttttct taaacaattt tactatttta tagggctct gatcctcttt   360 ttactaacga ttgaatgggt tgttcactac aaaagtacta ataaccttt attatcagca   420 acaatcattt tacattgcgt tttttggctc tttgcagggc tgaaatggaa aatgcgattt   480
tttacgatat ctgctatact aggactagta gtgttaggaa tttttggct ggggcgttaa   540

<210> SEQ ID NO 15
<211> LENGTH: 372
<212> TYPE: DNA
<213> ORGANISM: Artificial Sequence
<220> FEATURE:
<223> OTHER INFORMATION: Synthetic_BpOF4_13740 nucleic acid sequence

<400> SEQUENCE: 15
atgaaaggaa gaccactttt accatttgcg atcatagcaa ttgtcgggat tgttgttatg    60
atttcgcttt catttattgg gttaaaccag cgtgaagcga tgcaggcaga tgaagaagga   120
gaagaagaag taactgaaat tgaagatccg gtagcagctg gagaagaatt agtgcaaact   180
```

```
tcttgtatcg gttgtcacgg tggcgattta agcggtggtg caggtcctgc cctaacgtct    240
cttgaaggtc aatacactca agaagaaatt acagatattg ttgttaatgg gattggatca    300
atgccgtcag ttaacgataa cgaagtagaa gcagacgcaa ttgcacagta tttactatct    360
atttcagaat aa                                                        372
```

```
<210> SEQ ID NO 16
<211> LENGTH: 123
<212> TYPE: PRT
<213> ORGANISM: Artificial Sequence
<220> FEATURE:
<223> OTHER INFORMATION: Synthetic_BpOF4_13740 amino acid sequence

<400> SEQUENCE: 16
```

```
Met Lys Gly Arg Pro Leu Leu Pro Phe Ala Ile Ile Ala Ile Val Gly
1               5                   10                  15

Ile Val Val Met Ile Ser Leu Ser Phe Ile Gly Leu Asn Gln Arg Glu
            20                  25                  30

Ala Met Gln Ala Asp Glu Glu Gly Glu Glu Val Thr Glu Ile Glu
        35                  40                  45

Asp Pro Val Ala Ala Gly Glu Glu Leu Val Gln Thr Ser Cys Ile Gly
    50                  55                  60

Cys His Gly Gly Asp Leu Ser Gly Gly Ala Gly Pro Ala Leu Thr Ser
65                  70                  75                  80

Leu Glu Gly Gln Tyr Thr Gln Glu Glu Ile Thr Asp Ile Val Val Asn
                85                  90                  95

Gly Ile Gly Ser Met Pro Ser Val Asn Asp Asn Glu Val Glu Ala Asp
            100                 105                 110

Ala Ile Ala Gln Tyr Leu Leu Ser Ile Ser Glu
        115                 120
```

```
<210> SEQ ID NO 17
<211> LENGTH: 40
<212> TYPE: DNA
<213> ORGANISM: Artificial Sequence
<220> FEATURE:
<223> OTHER INFORMATION: Synthetic_F primer for sigB promoter

<400> SEQUENCE: 17
attgatgtgg atttctgcat tgcagcacct ggtgaggtgg                           40
```

```
<210> SEQ ID NO 18
<211> LENGTH: 25
<212> TYPE: DNA
<213> ORGANISM: Artificial Sequence
<220> FEATURE:
<223> OTHER INFORMATION: Synthetic_R primer for sigB promoter

<400> SEQUENCE: 18
aactggcctc ctaaattcgc ggttc                                           25
```

```
<210> SEQ ID NO 19
<211> LENGTH: 40
<212> TYPE: DNA
<213> ORGANISM: Artificial Sequence
<220> FEATURE:
<223> OTHER INFORMATION: Synthetic_F primer for BPOF4_13740

<400> SEQUENCE: 19
gcgaatttag gaggccagtt atgaaaggaa gaccactttt                           40
```

```
<210> SEQ ID NO 20
<211> LENGTH: 40
<212> TYPE: DNA
<213> ORGANISM: Artificial Sequence
<220> FEATURE:
<223> OTHER INFORMATION: Synthetic_F primer for BpOF4_05495

<400> SEQUENCE: 20
gcgaatttag gaggccagtt atgaaaaagt ttttattagc                            40

<210> SEQ ID NO 21
<211> LENGTH: 40
<212> TYPE: DNA
<213> ORGANISM: Artificial Sequence
<220> FEATURE:
<223> OTHER INFORMATION: Synthetic_R primer for BpOF4_05495

<400> SEQUENCE: 21
ttggtcaaac ctcccctcat ttattgagct tcaagccatg                            40

<210> SEQ ID NO 22
<211> LENGTH: 40
<212> TYPE: DNA
<213> ORGANISM: Artificial Sequence
<220> FEATURE:
<223> OTHER INFORMATION: Synthetic_F primer for BpOF4_05495

<400> SEQUENCE: 22
atctttagag gagacacaac atgaaaaagt ttttattagc                            40

<210> SEQ ID NO 23
<211> LENGTH: 42
<212> TYPE: DNA
<213> ORGANISM: Artificial Sequence
<220> FEATURE:
<223> OTHER INFORMATION: Synthetic_R primer for RBS insertion

<400> SEQUENCE: 23
ctgtgtttcc tcctttctcc tgttattctg aaatagatag ta                         42

<210> SEQ ID NO 24
<211> LENGTH: 42
<212> TYPE: DNA
<213> ORGANISM: Artificial Sequence
<220> FEATURE:
<223> OTHER INFORMATION: Synthetic_F primer for RBS insertion

<400> SEQUENCE: 24
caggagaaag gaggaaacac agatgaaaaa gttttattat gc                         42

<210> SEQ ID NO 25
<211> LENGTH: 280
<212> TYPE: DNA
<213> ORGANISM: Artificial Sequence
<220> FEATURE:
<223> OTHER INFORMATION: Synthetic_sigB promoter

<400> SEQUENCE: 25
tgcagcacct ggtgaggtgg ctgagccggt gattgaaaag attgcacaag gtttacgtga      60
gcgcggaatc accgtggaac aaggacgatt cggcgcaatg atgaaggtca catcggttaa     120
cgaaggcccc ttcaccgttt tggtcgagtg ctagccagtc aatcctaaga gcttgaaacg     180
ccccaatgtg ggggtgttaa gaactccata aaagcgcttg gaacttttt gtggaagcag      240 tccgttgaac ctcttgaacc gcgaatttag gaggccagtt                           280
```

```
<210> SEQ ID NO 26
<211> LENGTH: 366
<212> TYPE: DNA
<213> ORGANISM: Artificial Sequence
<220> FEATURE:
<223> OTHER INFORMATION: Synthetic_BPOF4_05495 nucleic acid sequence

<400> SEQUENCE: 26
atgaaaaagt ttttattagc tcttggcgca gttgttgctc ttacagcatg tggcggcgga        60
gacgaagctg ctccaccggt tgatgaggag tctccagcag tagatgaagc tccagcagat       120
gagcctgcag atgatgcaac agctggtgat tacgatgcag aatcagctcg tgctacatat       180
gagcaaagct gtatcgcatg tcatggcggc gatcttcaag gggcatcagg tccagctcta       240
gtaggaactg gcctgtcagc tgctgaaatt caagacatca tccaaaacgg acaaggttca       300
atgcctgctc aaaatttaga tgatgacgaa gctgctaacc tagctgcatg gcttgaagct       360
caataa                                                                  366

<210> SEQ ID NO 27
<211> LENGTH: 121
<212> TYPE: PRT
<213> ORGANISM: Artificial Sequence
<220> FEATURE:
<223> OTHER INFORMATION: Synthetic_BPOF4_05495 amino acid sequence

<400> SEQUENCE: 27

Met Lys Lys Phe Leu Leu Ala Leu Gly Ala Val Val Ala Leu Thr Ala
1               5                   10                  15

Cys Gly Gly Gly Asp Glu Ala Ala Pro Pro Val Asp Glu Glu Ser Pro
            20                  25                  30

Ala Val Asp Glu Ala Pro Ala Asp Glu Pro Ala Asp Asp Ala Thr Ala
        35                  40                  45

Gly Asp Tyr Asp Ala Glu Ser Ala Arg Ala Thr Tyr Glu Gln Ser Cys
    50                  55                  60

Ile Ala Cys His Gly Gly Asp Leu Gln Gly Ala Ser Gly Pro Ala Leu
65                  70                  75                  80

Val Gly Thr Gly Leu Ser Ala Ala Glu Ile Gln Asp Ile Ile Gln Asn
                85                  90                  95

Gly Gln Gly Ser Met Pro Ala Gln Asn Leu Asp Asp Asp Glu Ala Ala
            100                 105                 110

Asn Leu Ala Ala Trp Leu Glu Ala Gln
        115                 120
```